(12) United States Patent
Annonier et al.

(10) Patent No.: US 6,306,427 B1
(45) Date of Patent: Oct. 23, 2001

(54) PELLETS CONTAINING ACTIVE INGREDIENTS PROTECTED AGAINST DEGRADATION IN THE RUMEN OF RUMINANTS

(75) Inventors: Claude Annonier, Premilhat; Pierre Autant, Commentry; Jacques Ruel, Saint Gratien; Hugues Porte, Caluire; Jean-Claude Laffay, Marcillat; Alain Sabatier, Paris, all of (FR)

(73) Assignee: Rhone-Poulenc Nutrition Animale, Commentry (FR)

( * ) Notice: Subject to any disclaimer, the term of this patent is extended or adjusted under 35 U.S.C. 154(b) by 0 days.

(21) Appl. No.: 08/011,864

(22) Filed: Feb. 1, 1993

Related U.S. Application Data

(63) Continuation-in-part of application No. 07/892,134, filed on Jun. 2, 1992, now abandoned, which is a continuation-in-part of application No. 07/769,571, filed on Oct. 2, 1991, now abandoned, which is a continuation-in-part of application No. 07/638,554, filed on Jan. 9, 1991, now abandoned, application No. 08/011,864, which is a continuation-in-part of application No. 07/769,571, which is a continuation-in-part of application No. 07/638,554, application No. 08/011,864, which is a continuation-in-part of application No. 07/638,554.

(30) Foreign Application Priority Data

Jan. 9, 1990 (FR) .................................................. 89 17305
Jun. 28, 1991 (FR) .................................................. 91 08044

(51) Int. Cl.[7] ................................ A23K 1/18; A61K 9/16
(52) U.S. Cl. ........................ 424/438; 424/482; 424/442; 424/451; 424/469; 424/484; 424/485; 424/488; 514/965

(58) Field of Search ...................................... 424/438, 482, 424/442, 451, 469, 484, 485, 488; 514/965

(56) References Cited

U.S. PATENT DOCUMENTS

| | | |
|---|---|---|
| 3,413,118 | 11/1968 | Kviesitis . |
| 4,066,754 | 1/1978 | Chou . |
| 4,181,708 | 1/1980 | Dannelly . |
| 4,181,709 * | 1/1980 | Dannelly et al. . |
| 4,181,710 | 1/1980 | Dannelly et al. . |
| 4,780,315 * | 10/1988 | Wu et al. . |
| 4,876,097 | 10/1989 | Autant et al. . |
| 4,904,473 * | 2/1990 | Schricker et al. . |
| 4,948,589 * | 8/1990 | Iijima et al. . |
| 5,152,995 * | 10/1992 | Runkel et al. . |
| 5,219,572 * | 6/1993 | Sivaramakrishnan . |

FOREIGN PATENT DOCUMENTS

| | | |
|---|---|---|
| 1220663 | 4/1987 | (CA) . |
| 0 100 974 | 2/1984 | (EP) . |
| 0231817 | 1/1987 | (EP) . |
| 2656772 | 7/1991 | (FR) . |

* cited by examiner

*Primary Examiner*—Raj Bawa
(74) *Attorney, Agent, or Firm*—Finnegan, Henderson, Farabow, Garrett & Dunner, L.L.P.

(57) ABSTRACT

The invention relates to a composition, in pellet form, useful for the nutritional and/or medicinal supplementation of ruminants and a method for admixing the pellets with foodstuff. The pellet contains granules of one or more active ingredients/principles protected against degradation in toe rumen and one or more binding agents capable of being solubilized, crosslinked or melted. Optionally, the pellet may also contain an unprotected active ingredient for release in the rumen. The pellet may further contain a disintegrating agent and/or filler.

76 Claims, No Drawings

PELLETS CONTAINING ACTIVE INGREDIENTS PROTECTED AGAINST DEGRADATION IN THE RUMEN OF RUMINANTS

This is a continuation-in-part of the following U.S. patent applications: (1) Ser. No. 07/638,554, filed on Jan. 9, 1991 (abandoned); (2) Ser. No. 07/769,571, filed on Oct. 2, 1991 (abandoned), which is a continuation-in-part of Ser. No. 07/638,584, filed Jan. 9, 1991 (abandoned); and (3) Ser. No. 07/892,134, filed on Jun. 2, 1992 (abandoned), which is a continuation-in-part of Ser. No. 07/769,571, filed Oct. 2, 1991 (abandoned), which is a continuation-in-part of Ser. No. 07/638,554, filed Jan. 9, 1991 (abandoned).

The present invention relates to a process for the incorporation of active principles (i.e., active ingredients) into pellets and pellets made by such a process. It relates more particularly to the preparation of "special pellets" containing active principles protected against the enzymes of the rumen of ruminants, and optionally containing active ingredients unprotected with respect to degradation in the rumen. It also relates more particularly to the preparation of pellets intended for incorporation into the feed of ruminants.

"Pellet" means a nutrient unit or granule for animals obtained either by extrusion of a feed mixture through a die or by alternative pelletization techniques. Pellets are preferably in the form of rods, preferably cylindrical in shape, and have average sizes preferably from about 4 to 100 mm in length, more preferably 4 to 20 mm in length, and preferably from about 2 to 30 mm in diameter, more preferably 4 to 10 mm in diameter. These pellet sizes are preferred because they are easy to handle and administer and because they are not dust-forming.

The present invention is capable of solving the prior art problems associated with the incorporation of "granules" containing medicinal or nutritional compounds into "pellets" intended for incorporation into animal feed. These granules are incapable of undergoing conventional pelletization techniques due to sensitivity to temperature, pressure and shearing.

Pelletizing machines permit shaping by forcing a feed mixture through a perforated plate or die in the presence of steam. A feed mixture is passed through a perforated plate or die by means of a press. The press forces the feed mixture to be extruded through the holes in the perforated plate. On emerging from the perforated plate, the cylinders of feed mixture obtained are cut spontaneously or by a mechanical means. During the forced passage of the feed mixture through the die, products having low thermal resistance or mechanical strength undergo degradation due both to the pressure exerted and to the heat formed by friction and/or by the addition of steam. Steam promotes cohesion of the various meal or grain (floury) ingredients of the base feed mixture.

The problem has already been addressed in various earlier references. Among these earlier references is European patent application number EP 231,817 which describes a process for preparing "agglomerated feeds" based on vitamins or on compounds essential to human or animal health. Compounds having low thermal resistance or mechanical strength are often mixed with molasses and then undergo the action of steam in order to effect their cohesion and shaping. When these compounds undergo an increase in temperature during passage through pelletizing machines, they are at least partially destroyed due to the simultaneous action of steam and pressure.

EP 231,817 attempts to solve this problem in manufacturing such agglomerated feeds by spraying a solution or suspension of one or more vitamins, one or more drugs, and optionally a fat, onto a base core. This process only permits a coating of the base substance with the solution or suspension. This process is easy to carry out when using pulverulent or liquid products, such as vitamins or drugs. These products are easy to use in the form of a solution or suspension. However, the same does not apply when the product takes the form of larger agglomerated nutrient granules. When the material sensitive to heat and/or compression takes the form of granules having an average diameter of approximately 0.3 to 5 mm, as in the granules included in the pellets of the present invention, the aforementioned process is not easy to carry out.

French publication FR 2,338,653, describes a process for preparing feed-stuffs, onto which an enzyme suspension, preferably of proteases, in a liquid or molten fat, is sprayed. This process, similar to that taught in the European application referred to above, obtains "pellets" onto which the temperature-sensitive substance is deposited at the periphery by a spraying technique.

The problem which the present invention is capable of solving is to provide medicinal and/or nutritional additives, sometimes referred to herein as active principles or ingredients, which cannot be destroyed in the rumen of ruminants, in "special pellets" which are directly assimilable by the animals. The present invention also solves the problem of forming pellets directly assimilable by ruminant animals which contain medicinal and/or nutritional additives, such as amino acids and vitamins, protected against degradation in the rumen or paunch combined with such nutritional or medicinal additives present in an unprotected form.

The pellets of the invention are also capable of being mixed with conventional animal foodstuffs or ruminant feed pellets, whereby a homogeneous mixture of the pellets and conventional ruminant feed is maintained without separation.

In particular, the present invention provides pellets for use in the nutritional or medicinal supplementation of ruminants, each of the pellets comprising: granules of protected active principle, each of the granules having an average diameter of 0.3 to 5 mm and each of the granules comprising an active principle selected from vitamins, amino acids and drugs and a protective agent which protects the active principle from degradation in the rumen of ruminants, the granules of protected active principle being admixed with a binding agent capable of being solubilized, crosslinked or melted to form the pellets, the pellets being of a size, density and shape such that the pellets can be homogeneously maintained in admixture with conventional ruminant pellet feed, i.e., the pellets are miscible in all proportions with the conventional pellet feed. The pellets of the invention may also contain an active principle which is not protected from degradation in the rumen of ruminants.

Examples of the active-ingredient additives protected against degradation in the rumen include amino acids such as methionine and lysine, vitamins and also other nutritional or medicinal additives.

It is known that some amino acid supplementation is essential in the feeding of ruminants since some amino acids are limited in the ruminants' normal daily nutritional intake. These limited amino acids include methionine and lysine. These substances, when administered orally to ruminants, are destroyed in the rumen by the action of the digestive enzymes and microorganisms present in this organ. It has been discovered that, for the compounds to be utilizable by the animal and beneficial thereto, they must pass through the rumen without damage and disintegrate in or after the abomasum, so that the active substance may be released in the intestine and passed into the body. The product to be administered is protected with a substance which makes it capable of passing through the rumen without substantial damage but which allows disintegration in or after the abomasum.

Known coating compositions include a combination of a substance sensitive to pH variations, particularly a substance selected from synthetic basic copolymers, with at least one hydrophobic substance which may be selected, for example, from fatty acids or their derivatives and hydrophobic polymers. Such compositions are described in French Patents FR 78/23,966 (2,401,620), FR 78/23,968 (2,401,621) and FR 81/18,954 (2,514,261).

The main groups of coating agents include copolymers of vinylpyridine and styrene with a hydrophobic substance, preferably stearic acid and/or a water-insoluble polymer, for example ethylcellulose.

The group of coating agents involving enzymatic digestion includes chitosan and/or zein, combined with a hydrophobic substance, preferably stearic acid, and optionally a water-insoluble polymer, preferably ethylcellulose.

The granules which include protected active principles take the approximate form of spherical particles having a mean diameter of between about 0.3 and 5 mm, preferably 0.5 to 3 mm, particularly about 2 mm. Granules of this size are not conducive to being sprayed onto pellets or cores of nutrient material. These granules are also not conducive to being introduced into pelletizing machines because the coating undergoes attack by phenomena such as abrasion, shearing, temperature rise, and the addition of steam and pressure. These phenomena bring about at least partial degradation of the coating and hence create an instability of the active ingredients in the rumen upon being ingested by the animal.

Thus, heretofore it has appeared impossible to make ruminants ingest the protected active ingredients in a manner other than by dispersing granules of them in the feed, which creates problems of homogeneity, concentration and distribution.

The present invention provides a method for ruminant ingestion of protected active principle without general dispersion on the ruminants' feed. It comprises preparing special pellets containing granules of active principles protected against degradation in the rumen. These pellets are obtained by mixing the protected active ingredient in granular form with a binding agent selected from binding agents capable of being solubilized, binding agents capable of being crosslinked and binding agents capable of being melted. Optionally, the special pellets may contain unprotected active ingredients and/or a disintegrating agent and/or a filler.

Representative active principles protected against the action of the rumen which are useful in the invention include: essential amino acids, their salts, their derivatives and their analogues, preferably methionine and lysine; vitamins; and medicinal active ingredients or principles, such as antibiotics.

The binding agents which are useful in the special pellet of the present invention are preferably selected from feed materials permitting liquid/solid conversion to form a defined shape resembling that of a conventional feed pellet. Two classes of feed binding agents may be used: (i) binding agents used in a solvent or dispersant medium; and (ii) agents capable of being melted.

Binding agents of the first type used in a solvent or dispersant medium include: the class of hydrocolloids, preferably water-soluble derivatives of cellulose, more preferably carboxymethylcellulose, hydroxypropylcellulose, hydroxyethylcellulose, and hydroxymethylcellulose; the class of natural or synthetic polysaccharides, preferably gum arabic, gum tragacanth, carrageenates, dextrins, starch, xanthan gum, and alginates; sugars; molasses and vinasses; lignosulphonates; grain flours or seaweed meal; crystallizable inorganic compounds, preferably lime, plaster, sodium silicate, calcium carbonate and silica; gelatins; tanned proteins; polyvalent cation salts of natural or synthetic polyacids; and drying oils and mastics obtained by the combination of a drying oil and a filler.

Some binding agents are used with crosslinking agents. Preferred crosslinking agents include aldehydes for proteins, and salts or oxides of di- or trivalent metals for alginates, xanthan gum, molasses, vinasses and other hardening or curing agents suitable for the binders as known to those skilled in the art.

Binding agents of the second type capable of being melted include: fatty acids and alcohols; hydrogenated vegetable and animal fats; glycerol esters; paraffin waxes; natural and synthetic waxes; and synthetic polymers, preferably polyethylene glycols and polyvinyl acetate. Among all the binding agents, the most preferred are molasses, vinasses, fatty acids, hydrogenated vegetable or animal fats, plaster and paraffin waxes.

The following are examples of therapeutic or nutritional agents (active ingredients/principles) which are unprotected and which can be used in accordance with the present invention and are incorporated into the mixture to be subjected to shaping into pellets: mineral additives such as phosphorus, sulfur, magnesium, zinc, copper, cobalt, sodium, potassium, chlorine, iron, calcium, iodine, molybdenum, selenium, nickel and vanadium; vitamins such as vitamins A, B, D and E; energy-producing foods such as glucose, long-chain fatty acids and volatile fatty acids; yeasts; growth factors; enzymes such as ligninases and cellulases, for example, glucanases, xylanases, α-amylases, β-glucanases and phytases; elements of microbial flora such as lactobacilli, pediococci and streptococci; bacteria; fungi such as, for example, aspergilli and penicillia; peptides such as, in particular, growth hormone; and food adjuvants such as sodium bicarbonate, sorbitol, propylene glycol, betaine and sodium propionate.

Additives, e.g. fillers and disintegrating agents, may be used which provide the pellet with the desired qualities of density, mechanical strength and rapid disintegration in the rumen. Useful additives for the preparation of the special pellets according to the invention include: inorganic mineral additives, preferably silica, silicates, talc, clays, calcium carbonates and phosphates; and additives derived from natural products, preferably grain flours, residues of the cereals, wood, brewery and fermentation industries (waste- or by-products), ground feed cakes, cellulose vegetable fibers, polysaccharides and sugars.

The binding agent, supplemented where appropriate with additives, preferably represents 40 to 95% of the mass of the special pellet according to the invention. The content of inorganic or natural additives represents from 0 to 80% by weight relative to the binding agent.

The mixing of the binding agent and the protected product may be carried out prior to or at the same time as the shaping. The shaping may be carried out by means of a die or a mold.

The nature of the binding agent, the pouring temperature and the quantity of additives will be adapted by those skilled in the art to achieve the quality of the desired special pellet.

The properties which may be manipulated include: appetency (palatability), density, shape, size, mechanical resistance or strength, solubility, and ability to disintegrate in the rumen.

Pellets according to the present invention preferably take the form of rods, more preferably cylinders, possessing average dimensions of about 4 to 100 mm in length, more preferably 4 to 20 mm in length, and about 2 to 300 mm in diameter, more preferably 4 to 10 mm in diameter.

The special pellets according to the invention possess a plurality of features which make them useful for the feeding of ruminants:

(1) The special pellets are miscible in all proportions with traditional granulated feed, i.e., conventional ruminant pellet feed generally distributed to animals as a supplement to the basic feed (fodder) ration. That is, they can withstand, without unmixing or separation, the different steps of handling to which feed pellets are typically subjected. Thus the special pellets can become homogeneously integrated into the regular feed distribution system. Selection of a suitable shape and density of the pellets to obtain miscibility with the intended traditional ruminant feed pellets is within the purview of one skilled in the art.

(2) For the special pellets according to the present invention, loss of protection of the protected active principles is limited during shaping and mechanical destruction of the protected active ingredients is thus reduced.

(3) The special pellets produced according to the method of the present invention disintegrate rapidly in the rumen. They avoid a loss of protection of the active principles on mastication during rumination. The protected active principles are free to continue their passage with the unprotected active ingredients being released in the rumen and the protected active ingredients being stable against degradation in the rumen.

The extent of protection which characterizes the protected principles is equal to 100 minus the extent of release observed in vitro by measurement of the release of the active principles after 24 hours in 1,000 ml of buffer having a pH of 6, with stirring at 300 rpm at 40° C. The extent of release represents the percentage proportion of active principles released during the test. The size of the test sample is dependent on the nature of the active principle and its content. For the amino acids mentioned as examples, the test is carried out on approximately 6 g of equivalent. The extent of protection should be as high as possible.

The disintegration of the special pellets in the rumen, which permits release of the unprotected and protected active principles, is evaluated by incubation in the rumen of fistulated cattle by means of sachets made of nylon fabric with a mesh size of 350 microns. The disintegration time should be as short as possible, preferably less than 48 hours.

The present invention will be described more completely by means of the examples which follow. These examples are not to be considered limiting with respect to the invention, in particular with respect to either the protected active ingredients/principles or the binding agents used.

COMPARATIVE EXAMPLES I AND II AND EXAMPLES 1–12

In Comparative Examples I and II as well as Examples 1–12 in accordance with the invention, the pellets contain either Type A granules of protected active principles or Type B granules of protected active principles as described below. The protected active ingredients used for the examples are granules approximately 2 mm in diameter. In the examples, all percentages are by weight unless otherwise indicated.

Type A granules are made using particles of lysine monohydrochloride and methionine in a proportion of about 75:25 by weight, containing approximately 12% of a binding agent of a mixture of stearic acid containing 5% w/w of 2-vinylpyridine-co-styrene copolymer, and are protected against degradation in the rumen by a coating layer representing 16% by weight of the protected granules. The coating layer is composed of a mixture of 30% of 2-vinylpyridine-co-styrene copolymer, 60% of talc and 10% of stearic acid. The extent of protection of the Type A granules is 97%.

Type B granules are made from particles of lysine monohydrochloride and methionine in a proportion of about 75:25 by weight, containing approximately 12% of a binding agent of a mixture of stearic acid containing 5% w/w of 2-vinylpyridine-co-styrene copolymer, protected against degradation in the rumen by a coating layer representing 12% by weight of the protected product. The coating layer is composed of a mixture of 20% of 2-vinylpyridine-co-styrene copolymer, 60% of talc and 80% of stearic acid. The extent of protection of the Type B granules is 99%.

The Type A and B granules used for the feeding of ruminants are described in detail in U.S. Pat. No. 4,181,708, the disclosure of which is herein incorporated by reference, and in European Patent 260,186, the disclosure of which is also specifically incorporated by reference herein.

COMPARATIVE EXAMPLE I

Two % by weight of Type A granules were introduced into a mixture of grain flours (meals) intended for the feeding of livestock. This mixture was made into the form of granulated feed particles in a KAHL rotary die press after steam treatment in accordance with the traditional method of preparation of feeds. The product obtained took the form of extruded cylinders 5 mm in diameter and approximately 15 mm in length.

The extent of protection of the amino acids used for this comparative example was 0% in the granulated feed after passage through the press.

COMPARATIVE EXAMPLE II

Two % by weight of Type B granules were introduced into a mixture of flours intended for the feeding of livestock. This mixture was made into the form of granulated feed in a KAHL rotary die press after steam treatment in accordance with the traditional method of preparation of granulated feeds. The product obtained took the form of extruded cylinders 5 mm in diameter and approximately 15 mm in length.

The residual or extent of protection of the amino acids used for this comparative example was 0% in the granulated feed after passage through the press.

Comparative Examples I and II demonstrate that making this type of product into the form of a granulated feed pellets by traditional methods leads to substantially total degradation of the protection against degradation in the rumen. Consequently, this degradation leads to loss of efficacy for the feeding of ruminants.

EXAMPLE 1

Pellets containing active principles protected against degradation in the rumen, and miscible in all proportions with the traditional granulated feed, were obtained in the following manner: Type A granules containing protected active principles were introduced into the cavities of a mold. The cavities were frustoconical in shape, 20 mm in height and 8 mm and 10 mm in diameter at the ends.

A molten binding agent was injected under pressure into the porous structure of the particulate bed thus produced in each cavity.

The finished product was recovered by release from the mold after solidification of the binding agent upon cooling.

The binding agent used had the following composition:

| | |
|---|---|
| stearic acid | 33.33% |
| palmitic acid | 22.22% |
| calcium carbonate | 22.22% |
| fermentation residue | 22.22% |

(EUROLYSINE PL 73)

The extent of protection and the amino acid titre in the final product are given in Table I below.

EXAMPLE 2

Pellets containing Type A granules of active principles protected against degradation in the rumen, and miscible in all proportions with the traditional granulated feed, were obtained by the molding technique described in Example 1.

The binding agent used had the following composition:

| | |
|---|---|
| stearic acid | 30% |
| palmitic acid | 20% |
| glyceryl monostearate | 50% |

The extent of protection and the amino acid titre in the final product are given in Table I below.

EXAMPLE 3

Pellets containing Type A granules of active principles protected against degradation in the rumen, and miscible in all proportions with the traditional granulated feed, were obtained by the molding technique described in Example 1.

The binding agent used had the following composition:

| | |
|---|---|
| stearic acid | 16.67% |
| palmitic acid | 11.11% |
| glyceryl monostearate | 27.78% |

The extent of protection and the amino acid titre in the final product are given in Table I below.

EXAMPLE 4

Pellets containing Type A granules of active principles protected against degradation in the rumen, and miscible in all proportions with the traditional granulated feed, were obtained by mixing Type A granules with a binding agent.

The binding agent used had the following composition:

| | |
|---|---|
| plaster | 22.73% |
| calcium carbonate | 45.45% |
| water | 31.82% |

The mixture was made into the form of pellets measuring approximately 20 mm by 10 mm by pouring the mixture onto a non-adhesive support. The pellets were recovered after drying in an oven.

The extent of protection and the amino acid titre in the final product are given in Table I below.

EXAMPLE 5

Pellets containing Type A granules of active principles protected against degradation in the rumen, and miscible in all proportions with the traditional granulated feed, were obtained by mixing Type A granules with a binding agent.

The binding agent used had the following composition:

| | |
|---|---|
| plaster | 25.32% |
| monocrystalline cellulose | 18.99% |
| water | 55.70% |

The mixture was made into the form of pellets measuring approximately 20 mm by 10 mm by pouring the mixture onto a non-adhesive support. The pellets were recovered after drying in an oven.

The extent of protection and the amino acid titre in the final product are given in Table I below.

EXAMPLE 6

Pellets containing granules of Type B active principles protected against degradation in the rumen, and miscible in all proportions with the traditional granulated feed, were obtained by mixing Type B granules with a binding agent.

The binding agent used had the following composition:

| | |
|---|---|
| plaster | 29.41% |
| calcium carbonate | 58.82% |
| water | 41.18% |

The mixture was made into the form of pellets measuring approximately 20 mm by 10 mm by pouring the mixture onto a non-adhesive support. The pellets were recovered after drying in an oven.

The extent of protection and the amino acid titre in the final product are given in Table I below.

EXAMPLE 7

Pellets of granules containing Type B active principles protected against degradation in the rumen, and miscible in all proportions with the traditional granulated feed, were obtained by mixing Type B granules with a binding agent.

The binding agent used had the following composition:

| | |
|---|---|
| plaster | 25.32% |
| monocrystalline cellulose | 18.99% |
| water | 55.57% |

The mixture was made into the form of pellets measuring approximately 20 mm by 10 mm by pouring the mixture onto a non-adhesive support. The pellets were recovered after drying in an oven.

The extent of protection and the amino acid titre in the final product are given in Table I below.

EXAMPLE 8

Pellets of granules containing Type A active principles protected against degradation in the rumen, and miscible in all proportions with the traditional granulated feed, were obtained by mixing Type A granules with a binding agent.

The binding agent used had the following composition:

| | |
|---|---|
| beet molasses | 25.32% |
| calcium oxide | 23.08% |

The mixture was made into the form of pellets measuring approximately 20 mm by 10 mm, by pouring the mixture onto a non-adhesive support. The pellets were recovered after spontaneous curing.

The extent of protection and the amino acid titre in the final product are given in Table I below.

EXAMPLE 9

Pellets of granules containing Type A active principles protected against degradation in the rumen, and miscible in all proportions with the traditional granulated feed, were obtained by mixing Type A granules with a binding agent.

The binding agent used had the following composition:

| | |
|---|---|
| molasses | 71.43% |
| gelatin | 14.29% |
| water | 14.29% |

The mixture was made into the form of pellets measuring approximately 20 mm by 10 mm by pouring the mixture onto a non-adhesive support. The pellets were recovered after gelling.

The extent of protection and the amino acid titre in the final product are given in Table I below.

EXAMPLE 10

Pellets of granules containing Type B active principles protected against degradation in the rumen, and miscible in all proportions with the traditional granulated feed, were obtained by mixing Type B granules with a binding agent.

The binding agent used had the following composition:

| | |
|---|---|
| molasses | 71.43% |
| gelatin | 14.29% |
| water | 14.29% |

The mixture was made into the form of pellets measuring approximately 20 mm by 10 mm by pouring the mixture onto a non-adhesive support. The pellets were recovered after gelling.

The extent of protection and the amino acid titre in the final product are given in Table I below.

EXAMPLE 11

Pellets of granules containing Type B active principles protected against degradation in the rumen, and miscible in all proportions with the traditional granulated feed, were obtained by mixing Type B granules with a binding agent.

The binding agent used had the following composition:

| | |
|---|---|
| clay | 50% |
| soybean flour | 12.5% |
| 4% strength aqueous solution of CMC | 37.5% |
| (CMC = carboxymethylcellulose sodium salt) | |

The mixture was made into the form of pellet particles of about 8 mm diameter by extrusion through a die. The extruded strands thus obtained were dried in a ventilated oven and reduced to pellet units of about 20 mm in length.

The extent of protection and the amino acid titre in the final product are given in Table I below.

EXAMPLE 12

Pellets of granules containing Type B active principles protected against degradation in the rumen, and miscible in all proportions with the traditional granulated feed, were obtained by mixing Type B granules with a binding agent.

The binding agent used had the following composition:

| | |
|---|---|
| dolomite | 59.7% |
| soybean flour | 14.9% |
| 4% strength aqueous solution of CMC | 25.4% |
| (carboxymethylcellulose sodium salt) | |

The mixture was made into the form of pellet particles of about 8 mm diameter by extrusion through a die. The strands thus obtained were dried in a ventilated oven and reduced to pellet units of about 20 mm in length.

The extent of protection and the amino acid titre in the final product are given in Table I below.

Table I (which corresponds to Table I in Ser. No. 07/769,571, which table is incorporated by reference herein) summarizes the extent of protection observed for the protected active principles used in the above examples, after they were made into the form of the pellets of the invention. Table I also shows that a judicious choice of the composition of the binding agent enables the rate of disintegration of the granules in the rumen to be adjusted.

It should be understood that the method of forming special pellets by agglomeration in the presence of a binding agent described in the present invention may be applied to an extremely wide range of active principles protected against degradation in the rumen, by matching the physicochemical features of the binding agent to the nature of their protection. Particular attention should be paid to the pH of the binding agent, the temperature at which it is used and its compatibility or its solvent power with respect to the composition protecting the protected active principle in question.

TABLE I

Characteristics of the products produced:

| Example No. | Nature of the active principle protected | Level of A or B in the agglomerated final product % by weight | Extent of disintegration of the final product in the rumen after % by weight | | | Extent of protection of the active principle in the final product % |
|---|---|---|---|---|---|---|
| | | | 6 h | 24 h | 48 h | |
| 3 | A | 52 | | 40 | 100 | 93 |
| 4 | A | 65 | | 10 | 100 | 88 |
| 5 | A | 55 | | 10 | 60 | 92 |
| 6 | A | 29 | | | 15 | 86 |
| 7 | A | 42 | 100 | | | 99 |
| 8 | B | 28 | | | 100 | 65 |
| 9 | B | 48 | 100 | | | 93 |
| 10 | A | 35 | 100 | | | 91 |
| 11 | A | 56 | 100 | | | 89 |
| 12 | B | 40 | 100 | | | 83 |
| 13 | B | 37.5 | 100 | | | 99 |
| 14 | B | 37.5 | 100 | | | 89 |

COMPARATIVE EXAMPLE III AND EXAMPLES 13–19

In Comparative Example III and Examples 13–19 in accordance with the invention described below, the protected active ingredients used are Type C granules about 2 mm in diameter. In these examples, all percentages are by weight unless otherwise indicated.

Type C granules of protected active ingredients are particles of lysine monohydrochloride and methionine in a weight proportion of 75/25, and about 12% of a binder of a mixture of stearic acid containing 5% w/w of a 2-vinylpyridene/styrene copolymer. The particles are protected against degradation in the rumen by a coating layer representing 12% by weight of the granules. The coating is a mixture of 20% of a 2-vinylpyridene/styrene copolymer and 80% stearic acid. The extent of protection of these granules is 99%.

COMPARATIVE EXAMPLE III

Type C granules (2%) prepared above were introduced into a mixture of meals intended for animal feed and were shaped into a granulated feed in a KAHL rotary die press after treating with steam in accordance with a traditional method of preparing granulated feed pellets. The product obtained was in the form of extruded cylinders 5 mm in diameter and about 15 mm in length.

The residual level of protection in the granulated feed of the amino acids was 0% after passing through the press.

This comparative example shows that the shaping of this type of product into granulated feed pellets leads to total degradation in the rumen and subsequently to a loss of efficacy of the active ingredients in ruminant nutrition.

EXAMPLE 13

Pellets containing unprotected active ingredients, which are subject to destruction during pelletization, and granules of active ingredients protected against degradation in the rumen, miscible in all proportions with traditional granulated feed, were obtained by mixing the Type C granules and lactic acid bacteria (*Enterococcus faecium*) with a binder. The mixture had the following composition:

| | |
|---|---|
| dolomite | 36.3% |
| soybean meal | 9.0% |
| Type C granules | 29.0% |
| *Enterococcus faecium* containing $3 \times 10^{10}$ CFU/g | 3.1% |
| Water | 12.9% |
| Lignosulphite containing 42% water | 9.7% |

The mixture was prepared at 20° C. in a planetary mixer. The solid constituents were mixed in a dry state and the liquid binder was then introduced. Under these conditions, a moist paste is prepared very rapidly; the mixing time thus does not influence the quality of the final product.

The mixture was shaped into particles of about 8 mm in diameter by extrusion at 20° C. in a laboratory press with a 70 mm diameter piston driven by a screw through a die containing a compression cone 120 mm in length for an initial diameter of 70 mm and an opening 8 mm in diameter. The characteristics of this equipment make it possible to avoid breaking of the granules of protected active ingredients.

The pellets thus obtained were dried in a ventilated oven at 45° C. for 5 hours and reduced into elements about 20 mm in length.

The residual extent of protection of the protected active ingredients after maintaining for 24 hours in a solution at pH 6 remained unchanged (99.4%) in the final product. The amino acid titre was 19.2%. The level of bacteria remaining was $1.4 \times 10^8$ CFU/g of dry product. The operational yield on the enumeration of unprotected bacteria according to the counting method described below was 12.7%.

In the counting method, granules (100 g) are taken and added to tryptone salt (900 ml), and the mixture is stirred; this solution constitutes the solution with a dilution of −1. Successive dilutions of 1 ml in 9 ml are carried out to a dilution of $10^{-9}$. The medium used to carry out the counting is the MRS medium. The above dilutions (1 ml) are inoculated into the mass, and the counting is performed after incubating the plates for 48 hours at 37° C.

EXAMPLE 14

This example was prepared as in Example 13 above, except the mixture had the following composition:

| | |
|---|---|
| dolomite | 36.1% |
| soybean meal | 9.0% |
| Type C granules | 27.3% |
| Enterococcus faecium containing 1.7 × 10$^{10}$ CFU/g | 0.3% |
| Water | 18.2% |
| Lignosulphite containing 42% water | 9.1% |

The residual extent of protection of the Type C granules after 24 hours at a pH of 6 remained unchanged (99.4%) in the final product. The amino acid titre was 17.9%.

The level of bacteria remaining was 0.7×10$^8$ CFU/g of dry product. The yield on this operation on the enumeration of unprotected lactic acid bacteria was 20%.

EXAMPLE 15

This example was prepared as in Example 13 above, except the mixture had the following composition:

| | |
|---|---|
| dolomite | 19.8% |
| soybean meal | 9.9% |
| Type C granules | 34.3% |
| Enterococcus faecium containing 3 × 10$^{10}$ CFU/g | 9.3% |
| Water | 14.5% |
| Lignosulphite containing 42% water | 11.6 % |

The residual extent of protection of the Type C granules after 24 hours at a pH of 6 remained unchanged (99.4%) in the final product. The amino acid titre was 18.8%.

The level of bacteria remaining was 3.9×10$^8$ CFU/g of dry product. The operational yield on the enumeration of unprotected lactic acid bacteria was 11%.

EXAMPLE 16

This example was prepared as in Example 13 above, except the mixture had the following composition:

| | |
|---|---|
| dolomite | 29.3% |
| soybean meal | 7.5% |
| Type C granules | 29.5% |
| Enterococcus faecium containing 3 × 10$^{10}$ CFU/g | 11.8% |
| Water | 11.5% |
| Lignosulphite containing 42% water | 9.8% |

The residual extent of protection of the Type C granules after 24 hours at a pH of 6 remained unchanged (99.4%) in the final product. The amino acid titre was 19.4%.

The level of bacteria remaining was 5×10$^8$ CFU/g of dry product. The operational yield on the enumeration of unprotected lactic acid bacteria was 12%.

EXAMPLE 17

The procedure of Example 13 was followed, except the bacterium Enterococcus faecium was replaced with a Pediococcus pentosaceus strain containing 8×10$^{10}$ CFU/g.

The residual extent of protection of the Type C granules after 24 hours at a pH of 6 remained unchanged (99.4%) in the final product. The amino acid titre was 17.9%.

The level of bacteria remaining was 0.083×10$^8$ CFU/g of dry product. The operational yield on the enumeration of unprotected lactic acid bacteria was 0.28%.

EXAMPLE 18

The procedure of Example 13 was followed, except the bacterium *Enterococcus faecium* was replaced with a *Lactobacillus casei* subsp. *rhamnosus* strain containing 9.6×10$^9$ CFU/g.

The residual extent of protection of the Type C granules after 24 hours at a pH of 6 remained unchanged (99.4%) in the final product. The amino acid titre was 18.3%.

The level of bacteria remaining was 0.00029×10$^8$ CFU/g of dry product. The operational yield on the enumeration of unprotected lactic acid bacteria was of the order of 0.01%.

EXAMPLE 19

The procedure of Example 13 was followed, except the drying conditions were modified to be 5 hours at 55° C.

The residual extent of protection of the Type C granules after 24 hours at a pH of 6 remained unchanged (99.4%) in the final product. The amino acid titre was 19.8%.

The level of bacteria remaining was 0.4×10$^8$ CFU/g of dry product. The operational yield on the enumeration of unprotected lactic acid bacteria was 3.6%.

We claim:

1. Pellets for use in the nutritional or medicinal supplementation of ruminants, each of the pellets comprising an admixture including:
   (a) granules of protected active principle, each of the granules having an average diameter of 0.3 to 5 mm and comprising an active principle selected from the group consisting of vitamins, amino acids and drugs and a protective agent which protects the active principle from degradation in the rumen of ruminants, and
   (b) a binding agent capable of being solubilized, crosslinked or melted,
       said pellets being of a size, density and shape such that said pellets can be homogeneously maintained in admixture with ruminant pellet feed.

2. The pellets of claim 1, wherein the protective agent comprises a pH-sensitive copolymer or an enzymatically-degradable agent.

3. The pellets of claim 2, wherein the protective agent comprises a pH-sensitive copolymer.

4. The pellets of claim 3, wherein the pH-sensitive copolymer is a copolymer of vinylpyridine and styrene in combination with a hydrophobic agent.

5. The pellets of claim 2, wherein the protective agent comprises an enzymatically-degradable agent.

6. The pellets of claim 5, wherein the enzymatically-degradable agent is zein or chitosan.

7. The pellets of claim 1, wherein the binding agent is a binding agent capable of being crosslinked.

8. The pellets of claim 7, wherein the binding agent capable of being crosslinked comprises a hydrocolloid selected from the group consisting of alginates, gelatins, cellulose derivatives, polysaccharides, molasses and vinasses.

9. The pellets of claim 7, wherein said binding agent capable of being crosslinked is selected from the group consisting of proteins, alginates, xanthan gum, molasses, and vinasses, and the pellets further comprise a crosslinking agent selected from the group consisting of aldehydes for proteins, and salts and oxides of di- and trivalent metals for alginates, xanthan gum, molasses and vinasses.

10. The pellets of claim 1, wherein the binding agent is a binding agent capable of being melted.

11. The pellets of claim 10, wherein the binding agent capable of being melted is a member selected from the group consisting of fatty acids, fatty alcohols, glycerol esters, polyethylene glycols, paraffin waxes, natural and synthetic waxes, and hydrogenated animal and vegetable fats.

12. The pellets of claim 1, further comprising a disintegrating agent.

13. The pellets of claim 12, wherein the disintegrating agent is selected from the group consisting of grain flours, ground feed cakes, brewery and fermentation residues, cereal by-products and cellulose fibers.

14. The pellets of claim 12, further comprising a filler.

15. The pellets of claim 1, further comprising a filler.

16. The pellets of claim 1, where in each of said granules comprises a core containing said active principle, wherein said core is coated with said protective agent.

17. The pellets of claim 1, wherein the protective agent comprises chitosan.

18. Pellets for use in the nutritional or medicinal supplementation of ruminants, each of the pellets comprising an admixture including:
  (a) granules of protected active principle, each of the granules having an average diameter of 0.3 to 5 mm and comprising an active principle selected from the group consisting of vitamins, amino acids and drugs and a protective agent which protects the active principle from degradation prior to contact in the abomasum, and
  (b) a binding agent capable of being solubilized, crosslinked or melted, said pellets being of a size, density and shape such that said pellets can be homogeneously maintained in admixture with ruminant pellet feed,
    whereby the active principle is not degraded prior to contact in the abomasum.

19. The pellets of claim 18, wherein the protective agent comprises a pH-sensitive copolymer or an enzymatically-degradable agent.

20. The pellets of claim 19, wherein the protective agent comprises a pH-sensitive copolymer.

21. The pellets of claim 20, wherein the pH-sensitive copolymer is a copolymer of vinylpyridine and styrene in combination with a hydrophobic agent.

22. The pellets of claim 19, wherein the protective agent comprises an enzymatically-degradable agent.

23. The pellets of claim 22, wherein the enzymatically-degradable agent is zein or chitosan.

24. The pellets of claim 18, wherein the binding agent is a binding agent capable of being crosslinked.

25. The pellets of claim 24, wherein the binding agent capable of being crosslinked is selected from the group consisting of alginates, gelatins, cellulose derivatives, polysaccharides, molasses and vinasses.

26. The pellets of claim 24, wherein said binding agent capable of being crosslinked is selected from the group consisting of proteins, alginates, xanthan gum, molasses and vinasses, and the pellets further comprise a crosslinking agent selected from the group consisting of aldehydes for proteins, and salts and oxides of di- and trivalent metals for alginates, xanthan gum, molasses and vinasses.

27. The pellets of claim 18, wherein the binding agent is a binding agent capable of being melted.

28. The pellets of claim 27, wherein the binding agent capable of being melted is selected from the group consisting of fatty acids, fatty alcohols, glycerol esters, polyethylene glycols, paraffin waxes, natural and synthetic waxes, and hydrogenated animal and vegetable fats.

29. The pellets of claim 18, further comprising a disintegrating agent.

30. The pellets of claim 29, wherein the disintegrating agent is selected from the group consisting of grain flours, ground feed cakes, brewery and fermentation residues, cereal by-products and cellulose fibers.

31. The pellets of claim 29, further comprising a filler.

32. The pellets of claim 18, further comprising a filler.

33. The pellets of claim 18, wherein each of said granules comprises a core containing said active principle, wherein said core is coated with said protective agent.

34. The pellets of claim 18, wherein the protective agent comprises chitosan.

35. A method of medicinal or nutritional supplementation of ruminants comprising:
  adding to pellet feed for ruminants pellets containing granules of a protected active principle, each of the granules having an average diameter of 0.3 to 5 mm and comprising an admixture including
    (a) an active principle selected from the group consisting of vitamins, amino acids and drugs and a protective agent which protects the active principle from degradation prior to contact in the abomasum, and
    (b) a binding agent capable of being solubilized, crosslinked or melted, said pellets being of a size, density and shape such that said pellets can be homogeneously maintained in admixture with the pellet feed,
  whereby the active principle is not degraded prior to contact in the abomasum.

36. The method of claim 35, wherein the protective agent comprises a pH-sensitive copolymer or an enzymatically-degradable agent.

37. The method of claim 36, wherein the protective agent comprises a pH-sensitive copolymer.

38. The method of claim 37, wherein the pH-sensitive copolymer is a copolymer of vinylpyridine and styrene in combination with a hydrophobic agent.

39. The method of claim 36, wherein the protective agent comprises an enzymatically-degradable agent.

40. The method of claim 36, wherein the protective agent comprises zein or chitosan.

41. The method of claim 35, wherein the binding agent is a binding agent capable of being crosslinked.

42. The method of claim 41, wherein the binding agent capable of being crosslinked is a hydrocolloid selected from the group consisting of alginates, gelatins, cellulose derivatives, polysaccharides, molasses and vinasses.

43. The method of claim 41, wherein said binding agent capable of being crosslinked is selected from the group consisting of proteins, alginates, xanthan gum, molasses, and vinasses, and the pellets further comprise a crosslinking agent selected from the group consisting of aldehydes for proteins, and salts and oxides of di- and trivalent metals for alginates, xanthan gum, molasses and vinasses.

44. The method of claim 35, wherein the binding agent is a binding agent capable of being melted.

45. The method of claim 44, wherein the binding agent capable of being melted is selected from the group consisting of fatty acids, fatty alcohols, glycerol esters, polyethylene glycols, paraffin waxes, natural and synthetic waxes, and hydrogenated animal and vegetable fats.

46. The method of claim 35, wherein the pellets further contain a disintegrating agent.

47. The method of claim 46, wherein the disintegrating agent is selected from the group consisting of grain flours, ground feed cakes, brewery and fermentation residues, cereal by-products and cellulose fibers.

48. The method of claim 46, wherein the pellets further contain a filler.

49. The method of claim 35, wherein the pellets further contain a filler.

50. The method of claim 35, wherein each of said granules comprises a core containing said active principle and further wherein said core is coated with said protective agent.

51. The method of claim 50, wherein the protective agent comprises chitosan.

52. A method of medicinal or nutritional supplementation of ruminants comprising:

adding to pellet feed for ruminants pellets comprising an admixture containing
  (a) granules of protected active principle, each of the granules having an average diameter of 0.3 to 5 mm and comprising an active principle selected from the group consisting of vitamins, amino acids and drugs and a protective agent comprising a pH-sensitive copolymer or an enzymatically-degradable agent which protects the active principle from degradation in the rumen, and
  (b) a binding agent capable of being solubilized, crosslinked or melted, said pellets being of a size, density and shape such that said pellets can be homogeneously maintained in admixture with said pellet feed.

53. The method of claim 52, wherein each of said granules comprises a core containing said active principle and further wherein said core is coated with said protective agent.

54. A method of forming a pellet for medicinal or nutritional supplementation of ruminants comprising the steps of:

(1) making a mixture including
  (a) granules of a protected active principle, each of the granules having an average diameter of 0.3 to 5 mm and comprising an active principle selected from the group consisting of vitamins, amino acids and drugs and a protective agent comprising a pH-sensitive copolymer or an enzymatically-degradable agent which protects the active principle from degradation in the rumen, and
  (b) a binding agent capable of being solubilized, crosslinked or melted; and
(2) forming the mixture, in the absence of steam, into a pellet containing said granules of protected active principle and said binding agent, said pellet being of a size, density and shape such that a plurality of said pellets can be homogeneously maintained in admixture with ruminant pellet feed.

55. The method of claim 54, further comprising adding a disintegrating agent to the mixture.

56. The method of claim 55, wherein the disintegrating agent is selected from the group consisting of grain flours, ground feed cakes, brewery and fermentation residues, cereal by-products and cellulose fibers.

57. The method of claim 55, further comprising adding a filler to the mixture.

58. The method of claim 54, further comprising adding a filler to the mixture.

59. The method of claim 54, wherein said forming includes die-extruding the mixture.

60. The method of claim 54, wherein said forming includes molding the mixture.

61. The method of claim 54, wherein said forming includes gelation of the mixture.

62. The method of claim 54, wherein each of said granules comprises a core containing said active principle and further wherein said core is coated with said protective agent.

63. The method of claim 54, wherein the protective agent comprises chitosan.

64. Pellets for use in the nutritional or medicinal supplementation of ruminants, said pellets having been produced by a process comprising the steps of:

(1) making a mixture containing
  (a) granules of a protected active principle, each of the granules having an average diameter of 0.3 to 5 mm and comprising an active principle selected from the group consisting of vitamins, amino acids and drugs and a protective agent which protects the active principle from degradation in the rumen, and
  (b) a binding agent capable of being solubilized, crosslinked or melted; and
(2) forming the mixture into pellets containing said granules of protected active principle and binding agent without degradation of the protected active principle, said pellets being of a size, density and shape such that said pellets can be homogeneously maintained in admixture with ruminant pellet feed.

65. The pellets of claim 64, wherein each of said granules comprises a core containing said active principle and further wherein said core is coated with said protective agent.

66. The pellets of claim 64, wherein the protective agent comprises chitosan.

67. Pellets for use in the nutritional or medicinal supplementation of ruminants comprising:

granules of protected active principle, each of the granules having an average diameter of 0.3 to 5 mm and comprising: (i) an active principle selected from the group consisting of vitamins, amino acids and drugs, and (ii) a protective agent for protecting the active principle against degradation in the rumen and subsequently releasing the active principle in the abomasum or the intestine; and a binding agent capable of being solubilized, crosslinked or melted;

wherein said pellets have been obtained by mixing the granules of protected active principle and the binding agent, said pellets being cylindrically shaped, 4–20 mm long and 4–10 mm in diameter, whereby said pellets can be homogeneously maintained in admixture with ruminant pellet feed.

68. The pellets of claim 67, wherein each of said granules comprises a core containing said active principle and further wherein said core is coated with said protective agent.

69. The pellets of claim 67, wherein the protective agent contains chitosan.

70. Pellets for use in the nutritional or medicinal supplementation of ruminants comprising:

granules of protected active principle, each of the granules having an average diameter of 0.3 to 5 mm and comprising an active principle selected from the group consisting of vitamins, amino acids and drugs, and a protective agent which protects the active principle from degradation in the rumen of ruminants;

an active ingredient unprotected against degradation in the rumen; and a binding agent admixed with said granules of protected active principle and said active ingredient, wherein said binding agent is a binding agent capable of being solubilized, crosslinked or melted;

wherein said pellets are of a size, density and shape such that said pellets can be homogeneously maintained in admixture with ruminant pellet feed.

71. The pellets according to claim 70, wherein the active ingredient unprotected with respect to the rumen comprises a member selected from the group consisting of minerals and trace elements, vitamins, glucose, fatty acids, yeasts, growth factors, enzymes, microbial flora, fungi, peptides, sodium carbonate, sorbitol, propylene glycol, betaine and sodium propionate.

72. The pellets according to claim 71, wherein the binding agent is a binding agent capable of being crosslinked comprising a hydrocolloid selected from the group consisting of alginates, gelatins, cellulose derivatives, polysaccharides, molasses and vinasses.

73. The pellets according to claim 72, further containing a crosslinking agent comprising aldehydes for proteins, or salts or oxides of di- or trivalent metals for alginates, xanthan gum, molasses and vinasses.

74. The pellets according to claim 71, wherein the binding agent is a binding agent capable of being melted comprising a member selected from the group consisting of fatty acids, fatty alcohols, glycerol esters, polyethylene glycols, paraffins, natural and synthetic waxes, and hydrogenated animal and vegetable fats.

75. The pellets according to claim 71, further containing a disintegrating agent selected from the group consisting of grain meals, ground oil-cake brewery and fermentation residues, cereal by-products and cellulose fibers.

76. The pellets according to claim 71, wherein the binding agent comprises a vegetable meal.

* * * * *